(12) United States Patent
Getman et al.

(10) Patent No.: US 7,858,141 B2
(45) Date of Patent: Dec. 28, 2010

(54) METHOD OF CREATING A SUSTAINED SILICON-CONTAINING QUATERNARY AMMONIUM ANTIMICROBIAL AGENT WITHIN A POLYMERIC MATERIAL

(75) Inventors: Gerry D. Getman, McMurray, PA (US); Matt Bootman, Cannonsburg, PA (US); Donald Wagner, Jr., Bridgeville, PA (US); Thomas Ward, Hudson, FL (US)

(73) Assignee: Biosafe Inc., Pittsburgh, PA (US)

( * ) Notice: Subject to any disclaimer, the term of this patent is extended or adjusted under 35 U.S.C. 154(b) by 981 days.

(21) Appl. No.: 11/386,348

(22) Filed: Mar. 22, 2006

(65) Prior Publication Data

US 2006/0217515 A1    Sep. 28, 2006

Related U.S. Application Data

(60) Provisional application No. 60/702,201, filed on Jul. 25, 2005, provisional application No. 60/664,222, filed on Mar. 22, 2005.

(51) Int. Cl.
*B05D 3/00* (2006.01)
(52) U.S. Cl. .................. 427/2.1; 428/208; 428/323; 428/329; 428/331; 428/524; 428/537.5; 162/167; 106/2; 427/2.14; 427/2.24; 427/2.25; 427/212; 427/214; 427/256; 427/288
(58) Field of Classification Search ............ 106/2; 162/167; 428/323, 208; 156/272; 427/2.1
See application file for complete search history.

(56) References Cited

U.S. PATENT DOCUMENTS

| | | | |
|---|---|---|---|
| 3,560,385 A | 2/1971 | Roth | |
| 3,695,921 A | 10/1972 | Shepherd | |
| 3,730,701 A | 5/1973 | Isquith | |
| 3,794,736 A | 2/1974 | Abbott | |
| 3,814,739 A | 6/1974 | Takeda | |
| 3,860,709 A | 1/1975 | Abbott | |
| 3,888,728 A * | 6/1975 | Petrik et al. | 162/167 |
| 4,255,480 A * | 3/1981 | Scher et al. | 428/208 |
| 4,282,366 A | 8/1981 | Eudy | |
| 4,394,378 A | 7/1983 | Klein | |
| 4,408,996 A | 10/1983 | Baldwin | |
| 4,411,928 A | 10/1983 | Baldwin | |
| 4,414,268 A | 11/1983 | Baldwin | |
| 4,504,541 A | 3/1985 | Yasuda | |
| 4,605,564 A | 8/1986 | Kulla | |
| 4,614,675 A | 9/1986 | Ona et al. | |
| 4,615,937 A | 10/1986 | Bouchette | |
| 4,620,878 A | 11/1986 | Gee | |
| 4,631,273 A | 12/1986 | Blehm | |
| 4,675,347 A | 6/1987 | Mochizuki | |
| 4,692,374 A | 9/1987 | Bouchette | |
| 4,842,766 A | 6/1989 | Blehm | |
| 4,847,088 A | 7/1989 | Blank | |
| 4,865,870 A | 9/1989 | Hu | |
| 4,999,210 A | 3/1991 | Solomon | |
| 5,024,875 A | 6/1991 | Hill | |
| 5,053,048 A | 10/1991 | Pinchuk | |
| 5,064,613 A | 11/1991 | Higgs | |
| 5,069,899 A | 12/1991 | Witbourne | |
| 5,290,894 A | 3/1994 | Melrose | |
| 5,340,583 A | 8/1994 | Dziabo | |
| 5,358,688 A | 10/1994 | Robertson | |
| 5,359,104 A | 10/1994 | Higgs | |
| 5,399,737 A | 3/1995 | Park | |
| 5,411,585 A | 5/1995 | Avery | |
| 5,536,861 A | 7/1996 | Robertson | |
| 5,624,704 A | 4/1997 | Darouiche | |
| 5,753,733 A | 5/1998 | Eck | |
| 5,954,869 A | 9/1999 | Elfersy | |
| 5,959,014 A | 9/1999 | Liebeskind | |

(Continued)

FOREIGN PATENT DOCUMENTS

EP    0090577 A1    10/1983

(Continued)

OTHER PUBLICATIONS

Merker et al., "The Reaction of Alkyl Halides with Carboxylic Acids and Phenols in the Presence of Tertiary Amines", The Journal of Organic Chemistry, vol. 26, pp. 581 and 582 (1961).

(Continued)

*Primary Examiner*—Michael Barr
*Assistant Examiner*—Andrew Bowman
(74) *Attorney, Agent, or Firm*—Panitch Schwarze Belisario & Nadel LLP

(57) ABSTRACT

A method of imparting sustained antimicrobial properties throughout a material or substrate using an antimicrobial polymerizable silicon-containing quaternary ammonium salt monomer in a solvent to form a quaternary ammonium salt solution; and mixing the silicon-containing quaternary ammonium salt solution with at least a second monomer or a polymer or coating a solid polymer. Depending on the nature of the second monomer or polymer and the reaction conditions; a copolymer with the first monomer or a homopolymer will form, such that a polymeric material, substrate or formed plastic product comprising the copolymer or homopolymer or blended with the coated concentrate will have sustained antimicrobial properties. This method can be used to make formed plastic products, thin layer films and other products having sustained antimicrobial properties.

15 Claims, No Drawings

U.S. PATENT DOCUMENTS

| | | |
|---|---|---|
| 6,113,815 A | 9/2000 | Elfersy |
| 6,120,587 A | 9/2000 | Elfersy |
| 6,146,688 A | 11/2000 | Morgan |
| 6,221,944 B1 | 4/2001 | Liebeskind |
| 6,329,490 B1 | 12/2001 | Yamashita et al. |
| 6,376,696 B1 | 4/2002 | Raab |
| 6,469,120 B1 | 10/2002 | Elfersy |
| 6,572,926 B1 | 6/2003 | Morgan |
| 6,613,755 B2 | 9/2003 | Peterson et al. |
| 6,632,805 B1 | 10/2003 | Liebeskind |
| 6,762,172 B1 | 7/2004 | Elfersy |
| 6,790,910 B1 | 9/2004 | Sosna et al. |
| 2003/0096934 A1 | 5/2003 | Jost et al. |

FOREIGN PATENT DOCUMENTS

| | | |
|---|---|---|
| EP | 0351957 A2 * | 1/1990 |
| EP | 0415540 A1 | 3/1991 |
| WO | WO 94/13748 A1 | 6/1994 |
| WO | WO 97/42200 A1 | 11/1997 |
| WO | WO 00/54587 A1 | 9/2000 |

OTHER PUBLICATIONS

"The Handling and Use of AEGIS Microbe Shield™ Technology," Form 7E4, AEGIS Environments, Midland, MI USA, Rev. Oct. 2004, pp. 1-12.

Sauvet et al. "Biocidal Polymers Active by Contact. V. Synthesis of Polysiloxanes with Biocidal Activity" J. Appl. Polym. Sci. vol. 75, 2000, pp. 1005-1012.

* cited by examiner

METHOD OF CREATING A SUSTAINED SILICON-CONTAINING QUATERNARY AMMONIUM ANTIMICROBIAL AGENT WITHIN A POLYMERIC MATERIAL

CROSS-REFERENCE TO RELATED APPLICATIONS

This application claims the benefit of U.S. Provisional Patent Application No. 60/664,222, filed Mar. 22, 2005, and U.S. Provisional Patent Application No. 60/702,201, filed Jul. 25, 2005, the disclosures of which are hereby incorporated herein by reference in their entireties.

BACKGROUND OF THE INVENTION

This invention relates to a composition and to methods of creating a polymeric material or substrate (as defined hereinafter), preferably in the form of a formed plastic product, thin layer film, laminate, or a composite with a solvent-borne antimicrobial agent in order to eliminate microbial growth on or in the material or substrate.

More particularly, this invention relates to a novel way to form an antimicrobial homopolymer or copolymer with a polymeric substrate, such that it has a non-leaching antimicrobial property that is not dependent on leaching antimicrobial agents. The methods described herein may be used to prepare or treat biocompatible devices or other products and impart antimicrobial properties to polymeric substrates containing the antimicrobial agent throughout the polymeric substrate.

There has been a great deal of attention in recent years given to the hazards of bacterial contamination from potential everyday exposure. Noteworthy examples of such concerns include the fatal consequences of food poisoning due to certain strains of *Eschericia coli* being found within undercooked beef in fast food restaurants; *Salmonella* contamination causing sicknesses from undercooked and unwashed poultry food products; and illnesses and skin infections attributed to *Staphylococcus aureus, Klebsiella pneumoniae*, yeast, and other unicellular organisms. With such an increased consumer interest in this area, manufacturers have begun introducing antimicrobial agents within various everyday products and articles. For instance, certain brands of polypropylene cutting boards, liquid soaps, etc., all contain antimicrobial compounds. The most popular antimicrobial agent for such articles is triclosan. Although the incorporation of such a compound within liquid or certain polymeric media has been relatively simple, other substrates, including thin polyurethane films, have proven less accessible. Such compounds are highly desired for films to provide not only antimicrobial benefits, but also to control mildew and odors. In particular, such films are highly desired for utilization as fabric coatings, food preserving articles such as food containers and wrapping materials, both to prevent introduction of pathogens within the protected food items (i.e., meat, for example), as well as to destroy any bacteria or other pathogenic microorganisms retained within the food package prior to and possibly during storage, and the like.

As used herein, an "antimicrobial agent" is an agent that destroys or inhibits the growth of microorganisms, and particularly pathogenic microorganisms. The major classes of microorganisms are bacteria, fungi including mold and mildew, yeasts, and algae. Microorganisms can be found in the air, the water, in and on the human body and bodies of animals, soil, wastes, and on all surfaces. The microorganisms are deposited from the air, food and drink spills, dust, dirt and tracked in soil, and from human and animal excreta such as sweat, urine, and feces. Organisms grow and multiply when there is available a nutrient source of food such as organic or inorganic material contained in such wastes, dirt, dust, and living tissue. For growth and multiplication, most microorganisms also require warm temperatures, and moisture. When these conditions exist, microorganisms multiply, grow and flourish. Microbial growth, however, leads to many problems, such as unpleasant odors ranging from stale to musty and mildew-like, to putrid and foul smelling, resembling ammonia. The growths also produce unsightly stains, discoloration, and deterioration of many surfaces and materials in which they come into contact. A more serious disadvantage of microbial growth is the proliferation of pathogenic microorganisms, their metabolic products and their somatic and reproductive cell parts, which contribute to the spread of disease, infection, and health disorders.

Although triclosan and other organic compounds have been taught for such purposes, due to migration concerns and potential health issues with such organic based compounds and compositions, such antimicrobial agents are now avoided, particularly when in potential contact with human skin or items for human consumption.

Discoloration of the films themselves is to be avoided in order to provide a relatively clear storage article. Yellowing or browning is highly discouraged in this sense. The utilization of silver-containing compounds in the past has presented certain potential problems with discoloration, such that improvements in this area are highly desired as well.

Silicon-containing quaternary ammonium salts having the following Formula I are recognized antimicrobial agents:

$$R_3N^+R^0{}_nSiX_{4-n}Y^- \qquad (I)$$

wherein each R and each $R^0$ is independently, a non-hydrolysable organic group; each X is, independently, a hydrolysable group; n is an integer of 1 to 3; and Y is a suitable anionic moiety to form the salt of the compound of Formula I.

The use of such silicon-containing quaternary ammonium salts in solvents adsorbed by a polymeric substrate surface where the quaternary salt is subsequently polymerized such that an interpenetrating network is formed within the interstices only of the polymeric substrate surface has been described in U.S. Pat. Nos. 6,146,688 and 6,572,926, the disclosures of which are hereby incorporated herein by reference.

Despite knowledge of the common usage of silicon-containing quaternary ammonium salts for imparting antimicrobial properties to surfaces, a method was not known for protecting surfaces through the use of antimicrobial agents polymerized throughout the entire substrate including throughout the bulk material used to make the substrate or throughout the thin layer film or laminate. The benefit of such a process and the products produced thereby is that antimicrobial protection is still available even if the surface is abraded or removed during the manufacture or use of a substrate or thin layer film or laminate. This is accomplished with the present invention.

The use of such silicon-containing quaternary ammonium compounds as antimicrobial agents in accordance with the prior art is well known and taught in a wide variety of U.S. patents, e.g., U.S. Pat. Nos. 3,560,385; 3,794,736; 3,814,739; 5,954,869; the disclosures of which are hereby incorporated herein by reference. It is also taught that these compounds possess certain antimicrobial properties, which make them valuable and very useful for a variety of surfaces, substrates, instruments and applications (see, e.g., U.S. Pat. Nos. 3,730, 701; 3,794,736; 3,860,709; 4,282,366; 4,394,378; 4,408,996; 4,414,268; 4,504,541; 4,615,937; 4,620,878; 4,631,273; 4,692,374; 4,842,766; 5,064,613; 5,358,688; 5,359,104; 5,411,585; 5,954,869; 5,959,014; 6,113,815; 6,120,587; 6,221,944; 6,469,120; 6,632,805; and 6,762,172; the disclosures of which are hereby incorporated herein by reference).

These silicon-containing quaternary ammonium antimicrobial compounds are available and widely used as disinfectants and biocides and to treat items that may undesirably support microbial growth. For example, silicon-containing quaternary ammonium salts are used to treat carpeting, walls, various commercial products such as sponges and fabrics, and even water. They are also used to rehabilitate "sick buildings," particularly after floods and water leaks, and reduce odors caused by mildew, fungi and bacterial growth in damp basement areas.

Most silicon-containing quaternary ammonium salts commercially available are generally pre-packaged in water or alcohol solutions of approximately 2-3 weight % or less quaternary salt concentration. They are applied to substrate surfaces, such as carpets, walls and floors, to kill the bacteria. The method of application often relies on delivering the silicon-containing quaternary ammonium salt in a fine spray. When treating fabrics, sponges, bedding, and similar products, the concentration of the quaternary ammonium salt generally can be much lower, e.g., less than 1 weight %.

More specifically, because hospital-acquired infections are the leading cause of hospital or long-term care infections, numerous attempts have been made to create antimicrobial surfaces in hospital and medical facilities. Most treatments rely on the use of antimicrobial washes to achieve a coated surface that is resistant to bacterial growth. Unfortunately, this indiscriminate use of antimicrobial agents results in the build up of increased resistance of bacteria and certain other microorganisms to the widely used antimicrobial agents. This presents a significant problem for those being treated in health care facilities, and particularly for immune-compromised patients.

Further, some antimicrobial surface treatments use a coating treatment that provides a vehicle for entrapping the antimicrobial agent on the surface but permit subsequent diffusion of the antimicrobial agent into the biological environment. Many such treatments rely upon a leaching mechanism to deliver the antimicrobial agent into the environment.

Thus, a method has not been devised to impart non-leaching, biocompatible, antimicrobial properties through out the entire substrate, thin film layer or laminate. Only the very surface has previously been made antimicrobial with a non-leaching antimicrobial agent through the formation of an interpenetrating network at the interface of the substrate surface and the antimicrobial agent, for only as deep into the surface as the antimicrobial agent could be adsorbed into the substrate. The present invention of making a homopolymer or copolymer of a silicon-containing quaternary ammonium salt of Formula I within a polymeric substrate, preferably in the form of a thin layer film or laminate, provides added benefits of sustained antimicrobial properties.

There has been a long-felt need to provide durable, reliable, long-lasting, non-leaching antimicrobial substrates, especially in the form of thin layer films and laminates, formed plastic products and composite materials that exhibit effective sustained antimicrobial characteristics throughout the substrate. Unfortunately, to date, no such substrates or materials were available that contained a non-leaching antimicrobial agent. The present invention satisfies this long-felt need.

Among other things, the present invention relates to a method for creating an antimicrobial agent for manufacture of medical devices and supplies that is biocompatible and antimicrobial throughout the entire composition of the device or supply.

The present invention also relates to a method for creating a biocompatible and antimicrobial material for use as or with building materials, paint thin films and consumer products.

The present invention further relates to an antimicrobial laminate counter top that is not dependent on leaching antimicrobial agents for surface microbial protection.

The present invention additionally provides a method for creating a copolymeric thin layer film or laminate having antimicrobial properties that can be applied to various medical and food supply surfaces.

BRIEF SUMMARY OF THE INVENTION

One aspect of the present invention relates to a method of imparting sustained antimicrobial properties to a copolymer comprising: (a) providing an antimicrobial first polymerizable silicon-containing quaternary ammonium salt monomer in a solvent to form a quaternary ammonium salt solution; (b) providing at least one of a second monomer and a polymer, each containing functionality that will react with the first silicon-containing quaternary ammonium salt monomer under reaction conditions whereby the first silicon-containing quaternary ammonium salt monomer is polymerized with at least one of the second monomer and the polymer to form a copolymer; and (c) reacting the silicon-containing quaternary ammonium salt solution with at least one of the second monomer and the polymer under reaction conditions whereby the first silicon-containing quaternary ammonium salt monomer is polymerized with at least one of the second monomer and the polymer to form a copolymer, such that the copolymer has sustained antimicrobial properties.

Another aspect of the present invention relates to a method of imparting sustained antimicrobial properties to a polymeric material comprising: (a) providing an antimicrobial first polymerizable silicon-containing quaternary ammonium salt monomer in a solvent to form a quaternary ammonium salt solution; (b) providing at least one of a second monomer and a polymer, each not containing functionality that will react with the first silicon-containing quaternary ammonium salt monomer; and (c) blending the silicon-containing quaternary ammonium salt solution with at least one of the second monomer and the polymer under conditions whereby the first silicon-containing quaternary ammonium salt monomer is polymerized to form a homopolymer that is blended with at least one of the second monomer and the polymer to form a blended polymer, such that the blended polymer has sustained antimicrobial properties.

Still another aspect of the present invention relates to a method of method of making a concentrate for a resin having sustained antimicrobial properties comprising: (a) providing an antimicrobial polymerizable silicon-containing quaternary ammonium salt monomer in a solvent to form a quaternary ammonium salt solution; (b) providing a solid polymer to be treated, wherein the solid polymer is in the form of at least one of powder, beads, pellets and flakes; (c) treating the solid polymer by one of spraying and slurrying the solid polymer without dissolving the solid polymer in the quaternary ammonium salt solution to thereby coat the solid polymer with the quaternary ammonium salt solution; and (d) drying the coated solid polymer to form the concentrate, wherein, when the concentrate is blended with a resin, the resin will have sustained antimicrobial properties.

The homopolymer, copolymer or coated polymer concentrate having the sustained antimicrobial properties may then be included with or coated upon any type of substrate or formed plastic product, such that the resulting substrate or formed plastic product also has sustained antimicrobial properties, at least throughout the coating, where a coating is applied.

DETAILED DESCRIPTION OF THE PREFERRED EMBODIMENTS

The method of the present invention uses the technology of reacting in solution an antimicrobial silicon-containing quaternary ammonium salt monomer with at least one of a second monomer or a polymer without or with functional groups that result in homopolymerization of the antimicrobial monomer in the absence of reactive functional groups on the second monomer or polymer, or copolymerization of the antimicrobial monomer with the functional groups of the second monomer or polymer. The homopolymer is blended with the second monomer or polymer as is another embodiment where a coated solid polymer is coated with a solution of the antimicrobial silicon-containing quaternary ammonium salt monomer. Optionally, but typically, the copolymer, homopolymer blended with resin and/or the coated solid polymer is blended with another resin or coated upon another substrate or article, where the resultant blended resin or substrate has sustained antimicrobial properties provided by the silicon-containing quaternary ammonium salt, and the coated article has sustained antimicrobial properties at least throughout the coating.

Definition of Terms

In addition to terms defined herein elsewhere, the following terms have the following definitions herein:

The article "a" or "an" includes not only the singular, but also the plural of the object to which the article relates.

"Bulk resin" means a resin in any form, such as pellets, beads, flakes or powder or the like, prior to forming into a product. Often additives are blended with the bulk resin prior to forming to impart such properties as: antimicrobial, antioxidation, UV resistance, color, fire retardance, etc.

"Formed plastic product" means a polymeric resin that has been formed into a shape using various molding, extrusion, pultrusion or other forming techniques.

"Polymer" means a large molecule built up by the repetition of small chemical units (monomers). The resulting chains can be linear, cyclic, branched or cross-linked into three-dimensional networks.

"Resin" means a synthetic polymeric plastic that may be thermoplastic or thermosetting.

"Substrate" means a product to which the antimicrobial silicon-containing quaternary ammonium salt is applied or with which it is mixed or otherwise blended or reacted to impart the substrate with sustained antimicrobial properties.

"Thermoplastic" polymer or resin means a polymer where no chemical bonds form with other chains. The polymer will melt with the addition of heat.

"Thermoset" polymer or resin means a polymer where chemical bonds form between chains resulting in a 3-dimensional cross-linked structure. These polymers do not melt.

The preferred antimicrobial silicon-containing quaternary ammonium salt used as the first monomer has a Formula I:

wherein each R and each $R^0$ is independently, a non-hydrolysable organic group; each X is, independently, a hydrolysable group; n is an integer of 1 to 3; and Y is a suitable anionic moiety to form the salt of the compound of Formula I.

Preferably, each R and each $R^0$ is independently a non-hydrolysable organic group, such as, without limitation, an alkyl group of 1 to about 22 carbon atoms or an aryl group, for example, phenyl; n is an integer of 1 to 3; each X is —OR', wherein R' is an alkyl group of 1 to about 22 carbon atoms, or an aryl group of 6 carbon atoms. More preferably, each of the R groups is independently methyl, ethyl, propyl, butyl, octyl, dodecyl, tetradecyl or octadecyl; each of the $R^0$ groups is independently methyl, ethyl, propyl, butyl, octyl, dodecyl, tetradecyl or octadecyl; and each X is —OR', wherein R' is methyl, ethyl, propyl or butyl; and even more preferably, methyl or ethyl. Preferably, Y is a suitable anionic moiety to form the salt of the polymer of Formula I, such as halide, hydroxyl, acetate, $SO_4^{-2}$, $CO_3^{-2}$ and a $PO_4^{-2}$ counter ion. More preferably, Y is a halide.

The presently most preferred silicon-containing quaternary ammonium salt is where two of the Rs are methyl and one R is octadecyl, $R^0$ is propyl, each X is a methoxy, n is 1 and Y is chloride, such that the monomeric quaternary ammonium salt is 3-(trimethoxysilyl) propyldimethyloctadecyl ammonium chloride.

Also preferably, the quaternary ammonium salt is selected from the group consisting of one of Formula II or III:

wherein each $R^1$ is, independently, halogen or $R^6O$, where $R^6$ is H, alkyl of 1 to about 22 carbon atoms, acetyl, acetoxy, acyl, propylene glycol, ethylene glycol, polyethylene glycol, polypropylene glycol; block and copolymers of ethylene and propylene glycol, an alkyl monoether of 1 to about 22 carbons of propylene glycol, ethylene glycol, polyethylene glycol, polypropylene glycol; a block or copolymer of ethylene and propylene glycol or the monoester of a carbonic acid of 1 to about 22 carbons and propylene glycol, ethylene glycol, polyethylene glycol, polypropylene glycol; a block or copolymer of ethylene and propylene glycol; octyphenol; nonylphenol; or sorbitan ether;

$R^2$ is benzyl, vinyl or alkyl of 1 to about 22 carbon atoms;

$R^3$ and $R^4$ are, independently, lower alkyl alcohol of 1 to 6 carbon atoms, lower alkoxy of 1 to 6 carbon atoms, alkyl of 1 to about 22 carbon atoms; or $R^3$ and $R^4$ can, together, form a morpholine or cyclic or heterocyclic, unsaturated or saturated, five to seven-member ring of the Formula IV:

wherein k is an integer from 0 to 2, wherein $R^7$, where the ring is saturated, is $CH_2$, O, S, NH, $NH_2^+$, $NCH_2$ $CH_2$ $NH_2$, $NCH_2CH_2NH_3^+$, $NCH_2CH_2N(R^8)(R^9)$, $NCH_2CH_2N^+(R^8)(R^9)(R^{10})$, N(alkyl), N(aryl), N(benzyl), wherein each $R^8$, $R^9$, and $R^{10}$ is, independently, benzyl, polyether, lower alkyl alcohol of 1 to 4 carbon atoms, lower alkoxy of 1 to 4 carbon atoms, or alkyl of 1 to about 22 carbon atoms, and wherein $R^7$, where the ring is unsaturated, is CH, N, $N^+H$, $N^+$(alkyl), $N^+$(aryl), $N^+$(benzyl), $NCH_2N$, $N^+HCH_2N$, $N^+$(alkyl)$CH_2N$, $N^+$(aryl)$CH_2N$, or $N^+$(benzyl)$CH_2N$;

wherein the ring is unsubstituted or substituted with alkyl of 1 to 22 carbon atoms, ester, aldehyde, carboxylate, amide, thionamide, nitro, amine, or halide;

$R^5$ is lower alkyl alcohol of 1 to 6 carbon atoms, $CH_2C_6H_5$, polyether, alkyl, alkoxy, perfluoroalkyl, pefluoroalkylsulfonate or perfluoroalkylcarboxylate, wherein the alkyl, alkoxy, perfluoroalkyl, perfluoroalkylsulfonate or perfluoroalkylcarboxylate is of 1 to about 22 carbon atoms, or is a five to seven-member ring of Formula IV as described above; and $Y^-$ is a suitable anionic moiety to form the salt of the compound of Formula II or III, and preferably, such as halide, hydroxyl, acetate, $SO_4^{-2}$, $CO_3^{-2}$ and a $PO_4^{-2}$ counter ion, more preferably, a halide, such as chloride, bromide or iodide, and most preferably, chloride.

The method of the present invention creates a copolymer or a homopolymer or a coated resin using the antimicrobial silicon-containing quaternary ammonium salt. Thus, in the present embodiments, the copolymer, the monomer or polymer blended with the homopolymer or a resin blended with the coated solid polymer are used to create a substrate or formed plastic product that includes the antimicrobial agent throughout its entire structure and does not lose its antimicrobial properties if and when it is machined, abraded or otherwise formed into any desired product. That is, such substrates have long-lasting, non-leaching, antimicrobial properties not only on the surface, but also throughout the treated material or substrate. This is what is meant by the use of the term "sustained" in the title and elsewhere herein. Thus, whatever portion of the formed plastic product made according to the present invention becomes the surface of such product after machining, working or other forming or manufacturing process, the surface with which humans and animals have contact will be an antimicrobial surface. Such substrates made according to the present invention are not toxic to humans or animals using or with which the products of the present invention are used. Such products may include, for example without limitation, a thin layer film, a paint thin film for use with latex or other paints for painting any surface, a laminate, a medical product, a building material, such as a counter top, floor tile or wall covering, doorknob, toilet handle, packaging material, or any other product where antimicrobial properties are desired. If a product or article is coated with an antimicrobial material made as set forth herein, the coating would have sustained antimicrobial properties throughout the coating.

The method of the present invention uses as an antimicrobial agent in monomer form, a silicon-containing quaternary ammonium salt of Formula I, such as, without limitation, 3-(trimethoxysilyl)propyldimethyloctadecyl ammonium chloride. In one embodiment of a method of this invention, the process involves converting the hydrolysable groups to OH groups through hydrolysis. These groups will react with the second monomer or polymer containing functional groups such as but not limited to —OH derived from an alcohol, —C(O)OH, derived from an organic acid, —NCO derived from an isocyanate, —$NH_2$, —NH and —$C(O)OR^{11}$ derived from an ester, wherein $R^{11}$ may be an aliphatic group, a cycloaliphatic group or an aryl group. Examples of such groups, without limitation, include an aliphatic group, such as an alkyl group of 1 to about 22 carbon atoms, for instance methyl, ethyl, propyl, butyl, octyl or dodecyl; a cylcoaliphatic group, such as cyclopentane or cyclohexane; or an aryl group, such as phenyl. The resulting reaction product will be a copolymer comprising the antimicrobial silicon-containing quaternary ammonium salt monomer as part of the copolymer with the second monomer or polymer containing the reactive functional groups.

Copolymers are well known in the art. They are prepared in a variety of ways and the technical literature is replete with the technology for the manufacture of such materials. The most common way to create copolymers is by blending two or more monomers or polymers, which may be oligomers capable of further copolymerization, in an appropriate mixer of a type well-known to those skilled in the art, using such also well-known conditions as temperature, mixing time and mixing speed to obtain a blended copolymer.

After the silicon-containing quaternary ammonium salt monomer has been combined with the second monomer or polymer of the resin used to form the copolymerized antimicrobial product, the silicon-containing quaternary salt forms a copolymer with the host or second monomer or polymer. Such copolymerization preferably is achieved by mixing the solution of the silicon-containing quaternary ammonium salt with at least one of the monomer or polymer with a base, such as sodium hydroxide, potassium hydroxide, ammonium hydroxide, an aliphatic amine, a cycloaliphatic amine and an aryl amine, an acid, such as hydrochloric acid, sulfuric acid and acetic acid, or heat, or a combination of a base or acid and heat. The base and acid may have concentrations of about 0.1N to about 1N. An effective temperature for copolymerization is about 20° C. to about 300° C., preferably about 70° C. to about 200° C., and more preferably about 100° C. to about 150° C. In general, the greater the temperature, the less time it takes for the copolymer to form. Typically, but not exclusively, the reaction conditions are those used in the fabrication steps in which the substrate or formed plastic product made from the copolymer is made. This can include such well-known procedures as heat curing, injection molding, extrusion, pultrusion, or ambient cure conditions.

If no reactive functional groups are present in the second monomer or the polymer with which the antimicrobial silicon-containing quaternary ammonium salt monomer is mixed or blended, the Si—OH groups of the antimicrobial monomer will cause such monomer to homopolymerize, forming siloxane bonds (—Si—O—SI—). This occurs under the same conditions mentioned above with respect to the copolymerization with a second monomer or polymer having reactive functional groups, but since such reactive functional groups are not present, homopolymerization results. The homopolymer of the antimicrobial salt then blends with the second monomer or polymer to produce a blended polymer having sustained antimicrobial properties.

In the method of making a concentrate by coating a solid polymer as mentioned above, an antimicrobial polymerizable silicon-containing quaternary ammonium salt monomer in a solvent to form a quaternary ammonium salt solution is provided. The solid polymer to be treated, preferably in the form of powder, beads, pellets or flakes, is also provided. The solid polymer is treated by spraying or slurrying the solid polymer, without dissolving the solid polymer, in the quaternary ammonium salt solution to thereby coat the solid polymer with the quaternary ammonium salt solution. The coated solid polymer then has the solvent removed, such as by evaporation, typically by drying the coated solid polymer, preferably to a degree of dryness where the coated polymer particles are free-flowing, such as no more than about 10% by weight of any solvent remaining based on the weight of the dried product. The coated solid polymer made by this method is thus a concentrate that imparts sustained antimicrobial properties to any resin with which it is blended and preferably uniformly mixed, typically in a melt blending operation, such as molding, extrusion or pultrusion.

The homopolymer, copolymer or coated polymer concentrate may be included with any type of substrate or made into a formed plastic product, such that the resulting substrate or formed plastic product also has sustained antimicrobial properties. This may be accomplished by blending, typically with melting, to produce the formed plastic product.

Yet another method of imparting sustained antimicrobial properties to a resin substrate or any other article is by dissolving in a solvent the homopolymer, copolymer or coated solid polymer concentrate as described above to form a second solution. This second solution is then used to coat a resin substrate or another article, such as by dipping the substrate or article with the second solution, spraying the substrate or article with the second solution, or rolling the second solution onto the substrate or article or with a roller. The solvent is then removed from the coated substrate or article, such as by evaporation, typically with drying. The resulting coated substrate or article has sustained antimicrobial properties throughout the entire coating.

The presence of the active antimicrobial silicon-containing quaternary ammonium group homopolymerized or copolymerized with the second monomer or polymer or in the coated solid polymer concentrate, or in or on a formed plastic product or a coated substrate or other article has been and may be substantiated by a dye test using Bromophenol blue. The longevity or permanence of the quaternary ammonium group has been demonstrated by dye testing the treated material or substrate after repeatedly challenging the treated host substrate with multiple hot (e.g., 140° F.) water rinses, aging treated samples with forced air or in a microwave oven, and subjecting the treated sample to repeated boiling water for 30 minutes.

The polymerized silicon-containing quaternary salt is "anchored" to the substrate polymer through chemical covalent bonding. The level of silicon-containing quaternary salt polymer should be less than about 5% by weight on the substrate to minimize adversely affecting properties of the host polymeric substrate. The amount of antimicrobial agent to the host monomer preferably is about 0.025% to about 0.5%, and more preferably about 0.1% to about 0.5%.

Preferably, the solvent is selected based on its ability to dissolve the host monomer. Exemplary solvents include, without limitation, water, methanol, ethanol, tetrahydrofuran, chloroform, carbon tetrachloride, ethylene glycol, propylene glycol and ethyl acetate.

Monomers with which the silicon-containing quaternary ammonium salt can be copolymerized to form antimicrobial copolymers according to this invention are, by way of example and not limitation, those used to form polyurethane, urea formaldehyde, melamine formaldehyde, polyvinyl pyrrolidone, polyvinyl alcohol, polyacrylates, polyamides, or polyesters. The polymers, themselves, having reactive functional groups, also may be reacted with the antimicrobial silicon-containing quaternary ammonium salt monomer.

An antimicrobial coating or thin layer film or laminate is formed when the copolymer solution or mixture of the silicon-containing quaternary ammonium salt and the host resin is applied to a surface and cured by solvent evaporation. Alternatively, a substrate, including substrate surfaces, onto which the antimicrobial copolymer is desired to be formed or into which it is desired to be impregnated could be dipped into the copolymer mixture. Such substrates could be paper, screens, glass or plastic plates or any other suitable substrate depending on the desired end use of the antimicrobial product. If a thin layer film or laminate is desired, it may have any desired dimensions, based on the available equipment used to make the product. Typically, but not exclusively, the thin layer or coating has a thickness of about 0.001 inch (0.025 mm) to about 3 inches (76.2 mm), preferably about 0.01 inch (0.25 mm) to about 1 inch (25.4 mm), and more preferably about 0.063 inch (1.6 mm) to about 0.25 inch (6.35 mm). Several layers could be made at the same time and pressed together to form a thicker layer or a laminated substrate. Multiple layers of the same material or different material can be formed into a laminate. Heat enhances the cure rate.

In addition, the present invention includes the additive, or preferably synergistic combination of antimicrobial agents comprising more than one silicon-containing quaternary ammonium salt as well as a combination of at least one silicon-containing quaternary ammonium salt with at least one other antimicrobial agent. Other antimicrobial agents may include, by way of example and not limitation, boric acid, a silver salt and a combination thereof.

Embodiments of the present invention will now be described in further detail with reference to the following specific, non-limiting examples.

Example 1

A 0.2% solution of 3-(trimethoxysilyl)propyldimethyloctadecyl ammonium chloride as the antimicrobial agent was prepared by dissolving 2 grams of 3-(trimethoxysilyl)propyldimethyloctadecyl ammonium chloride in 1,000 mL methanol. 200 grams of polyvinyl chloride resin beads were slurried with the antimicrobial methanol solution in a rotary evaporator. The methanol was removed with the use of heat and vacuum provided by a water aspirator. The methanol was recovered for reuse. The coated polyvinyl chloride resin was placed in a vacuum oven and heated to 120° C. for 30 minutes. The resin beads were dissolved in tetrahydrofuran and molded into a round disc with evaporation of the tetrahydrofuran in a vacuum oven. The round disc was tested for antimicrobial activity against $E.\ coli$.

Antimicrobial testing of the round disc was carried out essentially as described in the ASTM designation E 2149-01 entitled, "Standard test Method for Determining the Antimicrobial Activity of Immobilized Antimicrobial Agents under Dynamic Contact Conditions." This test is designed to evaluate the antimicrobial properties of materials, which contain active agents that are non-leaching. The method is described briefly below.

$E.\ coli$ was grown overnight in rich media in an incubator-shaker at 37° C. while shaking at 300 rpm. After 18 hours of incubation, the bacteria were removed from the incubator and the optical density at 660 nm was measured. The culture was diluted until the optical density corresponds to a bacterial concentration of between $1 \times 10^8$ and $3 \times 10^8$ Colony Forming Units (CFU) per milliliter. The bacteria were further diluted in phosphate buffer (0.3 mM $KPO_4$ at pH 7.2) such that the working concentration was $1 \times 10^6$ to $3 \times 10^6$ CFU/mL. Test specimens were added to sterile 15 mL test tubes followed by the addition of 3 mL of the bacterial solution. An aliquot was immediately removed from the flask, serially diluted, and used to inoculate Petri plates containing nutrient agar. The plates were incubated overnight and the concentration of bacteria (CFU/mL) was thus determined. This represents the Time 0 ($T_0$) control. The tube containing the sample was placed in a shaking incubator at 37° C. and 300 rpm for one hour, at which time another aliquot is taken and tested as above. This is the treated sample ($T_F$). All tests were controlled by the inclusion of a tube that contained an untreated sample and a flask with no sample but with bacteria. The controls demonstrate that the observed reduction in bacterial count is due to the applied material and not the mechanical stress or any property of the substrate material. Log kill is a standard method to establish the ability of antimicrobial agents to destroy microorganisms. A log kill of 5.0 means that 100,000 microorganisms were destroyed on contact with the treated surface. A log kill of 6.0 establishes that 1,000,000 microorganisms were destroyed on contact with the treated surface. A log kill in excess of 5.0 is typically interpreted as an exceptionally active antimicrobial agent. The disc was found to have a log kill of 6.5.

Example 2

Standard Test—Bromophenol Blue Testing

Successful treatment of the round disc made in Example 1 was verified by exposing the treated surface to Bromophenol blue, which colored the disc blue in the presence of quaternary ammonium compounds present on the surface.

Examples 3-5

The procedure of Example 1 was followed, except that the concentration of antimicrobial agent 3-(trimethoxysilyl)propyldimethyloctadecyl ammonium chloride was adjusted to produce antimicrobial polymeric substrates having concentrations of 0.05%, 0.1%, and 0.2% of the antimicrobial agent, respectively. All were effective in killing the E. coli bacteria.

Examples 6-11 reflect one way of producing antimicrobial melamine formaldehyde copolymers useful to make counter top laminates, floor tiles, or wall coverings, for instance.

Example 6

A 0.2% aqueous solution of 3-(trimethoxysilyl)propyldimethyloctadecyl ammonium chloride as the antimicrobial agent was prepared by dissolving 2 grams of 3-(trimethoxysilyl) propyldimethyloctadecyl ammonium chloride in 1,000 mL distilled water. The solution was allowed to age without stirring for one hour. This aqueous solution was used to make an antimicrobial copolymer resin solution with melamine formaldehyde (specifically 1,000 grams of the antimicrobial solution were mixed with 420 grams of CYMEL® 412 resin, available from Cytec Industries Inc., West Paterson, N.J.), to produce a copolymer having a concentration of 0.4 weight % of the antimicrobial agent in the copolymer. Kraft paper was impregnated with the above resin/antimicrobial agent solution until the paper was completely wetted with the resin/antimicrobial agent solution. Three layers of wetted paper were placed on top of each other and clamped together. The antimicrobial resin was allowed to copolymerize in an oven at 120° C. for a period of one hour. The resulting product was a thin film melamine formaldehyde laminate. Antimicrobial testing was carried out as described in Example 1. The laminate was found to exhibit a log kill of 5.6.

Example 7

Standard Test—Bromophenol Blue Testing

Successful treatment of the thin film laminate made in Example 6 was verified by exposing the treated surface to Bromophenol blue, which colored the copolymer substrate blue in the presence of monomeric or polymeric quaternary ammonium salt, thus confirming the presence in the copolymer of the antimicrobial silicon-containing quaternary ammonium moiety.

Examples 8-11

The procedure of Example 6 was followed, except that the concentration of the same antimicrobial agent, 3-(trimethoxysilyl)propyldimethyloctadecyl ammonium chloride, was adjusted to produce antimicrobial copolymers having concentrations of 0.05 weight %, 0.1 weight %, 0.2 weight % and 0.5 weight % of the antimicrobial agent, respectively. Bromophenol blue testing confirmed the presence in each instance of the antimicrobial agent in the copolymer laminate.

The method of the present invention has been shown to produce antimicrobial polymeric substrates that possess the ability to kill bacteria, fungi and molds. Table 1 shows the results of testing for effectiveness against E. coli the compositions made according to Examples 3-6, as well as testing of a composition having 0.5 weight % active antimicrobial agent after boiling for 10 minutes in water. Samples according to the present invention where the concentration of the active antimicrobial agent 3-(trimethoxysilyl)propyldimethyl octadecyl ammonium chloride was greater than 0.05% were effective in killing the E. coli bacteria.

TABLE 1

| Sample | Number of Survivors | Log Kill* |
|---|---|---|
| Controls | | |
| Laminate Control (untreated material) | $2.03 \times 10^6$ | NA |
| Spray Coated Laminate | 25 | 6.31 |
| Resin/Kraft Paper control** | $8.0 \times 10^4$ | NA |
| Resin/Active Antimicrobial Copolymer/Kraft Paper | | |
| 0.5% Active Antimicrobial | 0 | >4.90 |
| 0.2% Active Antimicrobial | 325 | 5.55 |
| 0.1% Active Antimicrobial | 375 | 5.55 |
| 0.05% Active Antimicrobial | $5.1 \times 10^5$ | NA |
| 0.5% Active Antimicrobial Boiled 10 Min | 50 | 5.55 |

Test Conditions: Dynamic Shake test
0.1 g Sample
$1 \times 10^5$ E. coli
1 Hour incubation
*Log kill is calculated using the control for each sample rather than the number added
**Note that the control either binds or kills a significant number of the input bacteria, which is believed to be due to residual formaldehyde in the controls It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. A method of imparting sustained antimicrobial properties throughout a copolymer substrate, the method comprising:
   (a) providing an antimicrobial first polymerizable silicon-containing quaternary ammonium salt monomer in a solvent to form a quaternary ammonium salt solution;
   (b) providing a bulk material comprising at least one of a second monomer and a polymer, each containing functionality that will react with the first silicon-containing quaternary ammonium salt monomer under reaction conditions whereby the first silicon-containing quaternary ammonium salt monomer is polymerized with at least one of the second monomer and the polymer of the bulk material to form a copolymer substrate; and
   (c) reacting the silicon-containing quaternary ammonium salt solution with at least one of the second monomer and the polymer of the bulk material under reaction conditions whereby the first silicon-containing quaternary ammonium salt monomer is polymerized with at least one of the second monomer and the polymer to form a copolymer substrate from the bulk material, such that the copolymer substrate has sustained antimicrobial properties throughout the substrate.

2. A method of making a bulk material concentrate for a resin substrate having sustained antimicrobial properties throughout the substrate, the method comprising:
(a) providing an antimicrobial polymerizable silicon-containing quaternary ammonium salt monomer in a solvent to form a quaternary ammonium salt solution;
(b) providing a bulk material solid polymer to be treated, wherein the solid polymer is in the form of at least one of powder, beads, pellets and flakes;
(c) treating the solid polymer by one of spraying and slurrying the solid polymer without dissolving the solid polymer in the quaternary ammonium salt solution to thereby coat the bulk material solid polymer with the quaternary ammonium salt solution; and
(d) drying the coated bulk material solid polymer to form the bulk material concentrate, wherein, when the bulk material concentrate is blended with a resin substrate, the resin substrate will have sustained antimicrobial properties throughout the substrate.

3. A method of making a blended resin substrate having sustained antimicrobial properties throughout the resin substrate, the method comprising:
(i) providing a bulk material concentrate according to claim 2;
(ii) providing at least one resin substrate for blending with the bulk material concentrate; and
(iii) blending the bulk material concentrate and the resin substrate to form a blended resin wherein the blended resin substrate has sustained antimicrobial properties throughout the substrate.

4. The method of claim 1 or 2, wherein the antimicrobial silicon-containing quaternary ammonium salt monomer has a Formula I:

$$R_3N^+R^0{}_nSiX_{4-n}Y^-  \qquad (I)$$

wherein each R and each $R^0$ is, independently, a non-hydrolysable organic group; each X is, independently, a hydrolysable group; n is an integer of 1 to 3; and Y is a suitable anionic moiety to form the salt of the compound of Formula I.

5. The method of claim 4, wherein $Y^-$ is selected from halide, hydroxyl, acetate, $SO_4^{-2}$, $CO_3^{-2}$ and a $PO_4^{-2}$ counterion.

6. The method of claim 5, wherein $Y^-$ is chloride, bromide or iodide.

7. The method of claim 4, wherein two of the Rs are methyl and one R is octadecyl, $R^0$ is propyl, each X is a methoxy, and n is 1.

8. The method of claim 4, wherein the quaternary ammonium salt is selected from the group consisting of one of Formula II and III, $$(R^1)_3SiR^2N^+(R^3)(R^4)(R^5)Y^- \qquad (II);$$

$$(R^1)_3SiR^2N(R^3)(R^4) \qquad (III);$$

wherein each $R^1$ is, independently, halogen or $R^6O$, where $R^6$ is H, alkyl of 1 to about 22 carbon atoms, acetyl, acetoxy, acyl, propylene glycol, ethylene glycol, polyethylene glycol, polypropylene glycol; block and copolymers of ethylene and propylene glycol, an alkyl monoether of 1 to about 22 carbons of propylene glycol, ethylene glycol, polyethylene glycol, polypropylene glycol; a block or copolymer of ethylene and propylene glycol or the monoester of a carbonic acid of 1 to about 22 carbons and propylene glycol, ethylene glycol, polyethylene glycol, polypropylene glycol; a block or copolymer of ethylene and propylene glycol; octyphenol; nonylphenol; or sorbitan ether;

$R^2$ is benzyl, vinyl or alkyl of from 1 to about 22 carbon atoms;

$R^3$ and $R^4$ are, independently, lower alkyl alcohol of 1 to 6 carbon atoms, lower alkoxy of 1 to 6 carbon atoms, alkyl of 1 to about 22 carbon atoms; or $R^3$ and $R^4$ can, together, form a morpholine or cyclic or heterocyclic, unsaturated or saturated, five to seven-member ring of the Formula IV:

$$-R^3-(R^7)_k-R^4- \qquad (IV)$$

wherein k is an integer from 0 to 2, wherein $R^7$, where the ring is saturated, is $CH_2$, O, S, NH, $NH_2^+$, $NCH_2CH_2NH_2$, $NCH_2CH_2NH_3^+$, $NCH_2CH_2N(R^8)(R^9)$, $NCH_2CH_2N^+(R^8)(R^9)(R^{10})$, N(alkyl), N(aryl), N(benzyl), wherein each $R^8$, $R^9$, and $R^{10}$ is, independently, benzyl, polyether, lower alkyl alcohol of 1 to 4 carbon atoms, lower alkoxy of 1 to 4 carbon atoms, or alkyl of 1 to about 22 carbon atoms, and wherein $R^7$, where the ring is unsaturated is, CH, N, $N^+H$, $N^+$(alkyl), $N^+$(aryl), $N^+$(benzyl), $NCH_2N,N^+HCH_2N,N^+$(alkyl)$CH_2N,N^+$(aryl)$CH_2N$, or $N^+$(benzyl)$CH_2N$;

wherein the ring is unsubstituted or substituted with alkyl of 1 to 22 carbon atoms, ester, aldehyde, carboxylate, amide, thionamide, nitro, amine, or halide;

$R^5$ is lower alkyl alcohol of 1 to 6 carbon atoms, $CH_2C_6H_5$, polyether, alkyl, alkoxy, perfluoroalkyl, pefluoroalkylsulfonate or perfluoroalkylcarboxylate, wherein the alkyl, alkoxy, perfluoroalkyl, perfluoroalkylsulfonate or perfluoroalkylcarboxylate is of 1 to about 22 carbon atoms, or is a five to seven-member ring of Formula IV; and $Y^-$ is a suitable anionic moiety to form the salt of the compound of Formula II or III.

9. The method of claim 4, wherein the silicon-containing quaternary ammonium salt monomer is 3-(trimethoxysilyl) propyldimethyloctadecyl ammonium chloride.

10. The method of claim 1, wherein the second monomer is one of a monomer selected from the group consisting of melamine formaldehyde, urea formaldehyde and epoxy and a monomer that contains functional groups selected from the group consisting of —OH derived from an alcohol, —C(O)OH, derived from an organic acid, —NCO derived from an isocyanate, —$NH_2$, —NH and —C(O)OR' derived from an ester, wherein R' is selected from the group consisting of an aliphatic group, a cyloaliphatic group and an aryl group.

11. The method of claim 1 or 2, wherein the solvent is selected from the group consisting of water, methanol, ethanol, tetrahydrofuran, chloroform, carbon tetrachloride, ethylene glycol, propylene glycol and ethyl acetate.

12. The method of claim 1 or 3, further comprising a forming the substrate having sustained antimicrobial properties throughout the substrate into a formed plastic product, such that the formed plastic product has sustained antimicrobial properties throughout the formed plastic product.

13. The method of claim 1 or 2 further comprising:
(i) dissolving in a solvent the copolymer substrate of claim 1 having sustained antimicrobial properties throughout the substrate or the bulk material concentrate of claim 2 to form a second solution;
(ii) coating an article with the second solution; and (iii) removing the solvent from the coated article; whereby the coated article has sustained antimicrobial properties throughout the coating.

14. The method of claim 13, wherein the step of coating the article is accomplished by at least one of dipping, spraying and rolling.

15. The method of claim 1, wherein the bulk material polymer reacted with the first monomer is melamine resin to form a copolymer substrate comprising melamine resin having sustained antimicrobial properties throughout the substrate, and the method further comprises forming a laminate made of the copolymer substrate comprising melamine resin used to impregnate a paper selected from the group consisting of Kraft paper and cellulose paper.

* * * * *